United States Patent [19]

Vogelbacher et al.

[11] Patent Number: 6,040,458
[45] Date of Patent: Mar. 21, 2000

[54] METHOD FOR PRODUCING N-SUBSTITUTED 3-HYDROXYPYRAZOLES

[75] Inventors: Uwe Josef Vogelbacher, Ludwigshafen; Michael Keil, Freinsheim; Ralf Klintz, Grünstadt; Josef Wahl, Schifferstadt; Horst Wingert, Mannheim; Hartmann König; Michael Rack, both of Heidelberg; Roland Götz; Joaquim Henrique Teles, both of Ludwigshafen, all of Germany

[73] Assignee: BASF Aktiengesellschaft, Ludwigshafen, Germany

[21] Appl. No.: 09/319,880
[22] PCT Filed: Dec. 4, 1997
[86] PCT No.: PCT/EP97/06780
§ 371 Date: Jun. 14, 1999
§ 102(e) Date: Jun. 14, 1999
[87] PCT Pub. No.: WO98/27062
PCT Pub. Date: Jun. 25, 1998

[30] Foreign Application Priority Data

Dec. 17, 1996 [DE] Germany .............. 196 52 516

[51] Int. Cl.[7] ................................................ C07D 231/22
[52] U.S. Cl. ........................................................ 548/371.1
[58] Field of Search ........................................... 548/371.1

[56] References Cited

U.S. PATENT DOCUMENTS 5,922,886  7/1999  König et al. .

FOREIGN PATENT DOCUMENTS 162 247   11/1985   European Pat. Off. .
97/03969   2/1997   WIPO .

OTHER PUBLICATIONS

J. Gen. Chem. USSR, Engl. Trans. 31, 1770 (1961).
Chem. Heterocycl. Comp. 5, 527 (1969).
J. Prakt. Chem. 313, 115 (1971).
J. Prakt. Chem. 318, 253 (1976).
J. Med. Chem. 1991, 34, 1560–1570.
J. Prakt. Chem. 313, 1118 (1971).

*Primary Examiner*—Robert W. Ramsuer
*Attorney, Agent, or Firm*—Keil & Weinkauf

[57] ABSTRACT

A process is described for preparing N-substituted 3-hydroxypyrazoles of the formula I

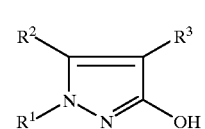

where $R^1$ is unsubstituted or substituted alkyl, alkenyl, alkynyl, cycloalkyl, aryl or heteroaryl and $R^2$, $R^3$ are hydrogen, cyano, halogen and unsubstituted or substituted alkyl, alkenyl, alkynyl, cycloalkyl, aryl or heteroaryl, by oxidizing a corresponding pyrazolidin-3-one.

14 Claims, No Drawings

METHOD FOR PRODUCING N-SUBSTITUTED 3-HYDROXYPYRAZOLES

The present invention relates to a process for preparing N-substituted 3-hydroxypyrazoles of the formula I

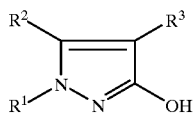

where
R$^1$ is unsubstituted or substituted alkyl, alkenyl, alkynyl, cycloalkyl, aryl or heteroaryl and
R$^2$,R$^3$ are hydrogen, cyano, halogen and unsubstituted or substituted alkyl, alkenyl, alkynyl, cycloalkyl, aryl or heteroaryl,
by oxidizing a pyrazolidin-3-one of the formula II.

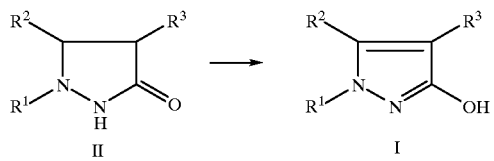

The literature discloses that N-substituted 3-hydroxypyrazoles are obtained by oxidizing corresponding pyrazolidinones [J. Gen. Chem. USSR, Engl. Trans. 31 (1961) 1770; Chem. Heterocycl. Comp. 5 (1969) 527; J. Prakt. Chem. 313 (1971) 115; J. Prakt. Chem. 318 (1976) 253; J. Med. Chem. 34 (1991) 1560; J. Prakt. Chem. 313 (1971) 1118; DE-A 34 15 385; PCT/EP 96/02,891].

As oxidizing agents in these processes, use is made of
elemental sulfur [J. Gen. Chem. USSR, Engl. Trans. 31 (1961) 1770],
elemental halogens [Chem. Heterocycl. Comp. 5 (1969) 527; J. Prakt. Chem. 318 (1976) 253; J. Prakt. Chem. 313 (1971) 1118],
peroxides [J. Med. Chem. 34 (1991) 1560; DE-A 34 15 385] and
Atmospheric oxygen [J. Prakt. Chem. 313 (1971) 115; J. Prakt. Chem. 313 (1971) 1118; PCT/EP 96/02,891].

With regard to industrial preparation of 3-hydroxypyrazoles, oxidation with elemental sulfur has the disadvantage that considerable amounts of sulfur reduction products are formed, which require complex work-up and disposal.

The use of elemental halogens is likewise unsuitable for an industrial synthesis of 3-hydroxypyrazoles, since the yields leave something to be desired and separating off the byproducts formed to a considerable extent is complex. Furthermore, the use of large amounts of elemental halogen as oxidizing agent is a disadvantage both for environmental reasons and also with regard to cost.

The known oxidation processes using peroxides require, on the one hand, complex purifications and only offer, on the other hand, an unsatisfactory yield with the use of expensive reagents, so that they are not suitable with regard to an industrial synthesis. The use of atmospheric oxygen as oxidizing agent [J. Prakt. Chem. 313 (1971) 115 and J. Prakt. Chem. 313 (1971) 1118] has the disadvantage that the reaction must be carried out in a strongly acidic medium. This gives rise to a considerable consumption of bases during work-up, resulting in a considerable production of salt, which is undesirable from the ecological aspect.

PCT/EP 96/02,891 describes oxidation using atmospheric oxygen in organic solution in the presence of iron salts and copper salts. However, in this process the oxidizing agent air forms explosive air/solvent vapor mixtures which are of concern for safety reasons and make stringent requirements of safety methods.

It is an object of the present invention to provide an economic and technically safe and simple process for preparing 3-hydroxypyrazoles.

We have found that this object is achieved by a process for preparing N-substituted 3-hydroxypyrazoles of the formula I

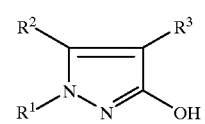

where
R$^1$ is unsubstituted or substituted alkyl, alkenyl, alkynyl, cycloalkyl, aryl or heteroaryl and
R$^2$,R$^3$ are hydrogen, cyano, halogen and unsubstituted or substituted alkyl, alkenyl, alkynyl, cycloalkyl, aryl or heteroaryl,
by oxidizing a pyrazolidin-3-one of the formula II

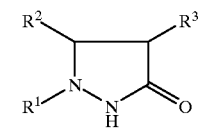

which comprises carrying out the reaction in water in the presence of a base using oxygen as oxidizing agent.

In the oxidation of the pyrazolidinones II, a procedure is generally followed in such a manner that an aqueous basic solution of II is treated with air or pure oxygen gas.

Suitable bases are inorganic or organic bases whose pK$_a$ is above 7.

The process according to the invention does not require complete deprotonation of the compound II. In the event of incomplete deprotonation of compound II, the pH of the reaction medium is below 7. Particularly advantageously, the process is carried out at pH>7. In this process the base is added to compound II at least in an equimolar amount.

Adding base increases the solubility of the pyrazolidinones to the extent that they are accessible for a reaction in water. To keep the carbon content of the reaction waste water very low, inorganic bases are preferred, such as hydroxides or carbonates of the alkali or alkaline earth metals, such as sodium hydroxide, potassium hydroxide, magnesium hydroxide, potassium carbonate or sodium carbonate. To avoid the solution becoming depleted in base when being treated with oxygen gas, nonvolatile bases are preferred.

Organic bases are equally suitable in principle. In this case, bases which are nonvolatile under reaction conditions are preferred not only for the abovementioned reasons, but also for safety reasons.

The process can be carried out in such a manner that the oxidation of the reaction mixture is accelerated by adding catalytic amounts of a metal salt. In most cases, this also increases the selectivity.

Suitable metal salts are, in particular, salts of iron in the divalent or trivalent oxidation state (eg. iron(II) chloride, iron(III) chloride, iron(II) sulfate, iron(III) sulfate, potassium hexacyanoferrate(II) and potassium hexacyanoferrate (III)), salts of copper in the monovalent or divalent oxidation state (eg. copper(I) chloride, copper(II) chloride, copper(I) sulfate and copper(II) sulfate), salts of cobalt in the divalent or trivalent oxidation state (eg. cobalt(II) acetate, cobalt(II) chloride and cobalt(III) fluoride), and also corresponding salts of main group or transition metals. A plurality of salts may also be used together as mixtures.

The metal salts are generally added in amounts of from 0.01 mol % to 20 mol %, preferably from 0.3 mol % to 10 mol %, in particular from 0.5 mol % to 5 mol %, based on II.

A preferred embodiment of the process according to the invention is oxidation using pure oxygen. In this case, the metal salt catalysis is unnecessary.

This oxidation is customarily performed at from 0° C. to the boiling point of the reaction mixture, preferably from 20° C. to 100° C. When the process is carried out under pressure, even higher temperatures are possible.

The process can be carried out at a pressure from 1 to 200 bar. The pressure can be built up by compressing air or pure oxygen or mixtures of these. Pressures of from 1 to 50 bar are advantageous. In particular, pressures of from 1 to 20 bar are suitable.

The reaction mixtures are worked up in a conventional manner, eg. by precipitating the product by neutralizing the reaction solution, with or without extraction, phase separation and with or without chromatographic purification of the crude products. Some of the intermediates and end products are produced in the form of colorless or slightly brownish, viscous oils, which are purified or freed of volatile portions under reduced pressure and at moderately elevated temperature. If the intermediates and end products are obtained as solids, the purification can be performed by recrystallization or digestion.

The process according to the invention is not restricted to compounds which are substituted in a defined manner, if the substituents are inert under the reaction conditions. Aliphatic radicals may be unbranched or branched. The chain length of the substituents is not critical for the process according to the invention, but for technical reasons, radicals having at most 10 carbons are usually chosen. Thus, alkyls generally contain from 1 to 10 carbons; alkenyls and alkynyls usually comprise from 2 to 10 carbons; and cycloalkyls contain from 3 to 10 ring members.

Aryl is, for example, phenyl or naphthyl;

heteroaryl is, for example, furyl, thienyl, pyrrolyl, isoxazolyl, isothiazolyl, pyrazolyl, oxazolyl, imidazolyl, pyridyl, pyridazinyl, pyrimidinyl or triazinyl;

halogen is chlorine, fluorine, bromine or iodine.

The substituents can bear other radicals inert under the reaction conditions; examples of these are:

halogen, cyano, $SO_3H$, COOH, alkyl, alkenyl, alkynyl, aryl or heteroaryl.

The 3-hydroxypyrazoles obtainable by the process according to the invention are suitable as intermediates for preparing dyes or active compounds in the pharmaceutical or plant protection sector.

COMPARATIVE EXAMPLES

1. Oxidation of pyrazolidinones using $FeCl_3$ [J.prakt.Ch. 313 (1991) 1118]

A solution of 23 g (0.142 mol) of $FeCl_3$ in 40 ml of $H_2O$ was added dropwise to a mixture of 14 g (0.071 mol) of 1-(4-chlorophenyl)pyrazolidin-3-one and 100 ml of 1 N HCl at about 25° C. After stirring overnight, 24 g of NaOH were added a little at a time; the mixture was heated to 90° C. and filtered with suction once hot. The precipitate was washed with boiling water.

After acidifying the filtrate to pH 5–6 and then extracting with $CHCl_3$, a small amount of a dark residue was obtained from the organic phase; no product could be detected in this residue.

No product of sufficient purity for quantitative or qualitative characterization could be isolated from the solid produced from the aqueous phase and from the filtration, either.

2. Oxidation of pyrazolidinones using $CuCl_2$ [J.prakt.Ch. 213 (1971) 115]

2.1. Oxygen was passed for 8 hours at 50° C. into a mixture of 19.6 g (0.1 mol) of 1-(4-chlorophenyl)pyrazolidin-3-one, 200 ml of 1 N HCl and 0.05 g of $CuCl_2 \times 2\ H_2O$ (0.293 mmol). The mixture was then stirred overnight and the resulting brown solid was filtered off with suction. 17.7 g of a mixture of pyrazolinone and pyrazolidinone in a ratio of 4:1 was obtained.

Calculated yield: 73%.

2.2. A similar experiment in which oxygen was passed in at 50° C. for 24 h produced 17.8 g of a mixture whose spectroscopic and physical data were identical with those obtained under 2.1. The thin-layer chromatographic analysis performed during the reaction showed that the amount of by-product increased constantly with the course of time. A further increase in the reaction time was therefore not studied.

3. Oxidation using chlorine gas 49.2 g of 1-(4-chlorophenyl)pyrazolidin-3-one were dissolved in 300 ml of methylene chloride. 18 g of chlorine gas were introduced slowly into the solution at 10° C. with cooling in an icebath. The reaction solution contained, according to HPLC (% peak area) approximately 70% of 1-(4-chlorophenyl)-3-hydroxypyrazole, 15% of starting material and 15% of 4-chloro-1-(4-chlorophenyl)-3-hydroxypyrazole.

4. Oxidation using bromine [Chem. Heterocycl. Comp. 5 (1969) 527]

49.2 g of 1-(4-chlorophenyl)pyrazolidin-3-one were dissolved in 300 ml of methylene chloride. 40 g of bromine were added slowly dropwise into the solution at 10° C. with cooling in an icebath. The reaction solution contained, according to HPLC (% peak area) approximately 76% of 1-(4-chlorophenyl)-3-hydroxypyrazole, 8% of starting material and 21% of 4-bromo-1-(4-chlorophenyl)-3-hydroxypyrazole.

PROCESS EXAMPLES ACCORDING TO THE INVENTION

5. Preparation of 1-(4-chlorophenyl)-3-hydroxy-4-methylpyrazole using air with Co(II) catalysis 92 g of 1-(4-chlorophenyl)-4-methylpyrazolidin-3-one and 1.3 g of cobalt(II) acetate×4 $H_2O$ were dissolved in the mixture of 700 ml of water and 43.1 g of potassium hydroxide (85%). The mixture was heated with stirring and air was passed through for seven hours at 80° C. After cooling, the reaction mixture was filtered, acidified with acetic acid to pH 5.5; the precipitate was filtered off with suction, washed with water and dried under reduced pressure. 78.9 g of a light solid, m.p. 214° C., were obtained.

6. Preparation of 1-(4-chlorophenyl)-3-hydroxypyrazole using air with potassium hexacyanoferrate(III) catalysis 98.3 g of 1-(4-chlorophenyl)pyrazolidin-3-one were dissolved in a mixture of 641.3 g of water and 33.75 g of potassium hydroxide and 0.98 g of potassium hexacyanoferrate(III) were added. The mixture was heated to 80° C., passing in a vigorous air stream through a capillary, and was then further oxidized at this temperature. After cooling, the mixture was acidified to pH 2 with concentrated sulfuric acid. The solid separating off was filtered off with suction, washed with water and diisopropyl ether and dried. 76 g of a light-brown solid remained.

7. Preparation of 1-(4-chlorophenyl)-3-hydroxypyrazole using air with Fe(III) catalysis 9.06 kg of 1-(4-chlorophenyl)pyrazolidin-3-one were dissolved in a mixture of 3.87 kg of potassium hydroxide and 73.6 kg of water and 90 g of iron(III) chloride were added. The mixture was heated to 80–85° C. and a vigorous air stream was passed in. After approximately 3 h, the reaction was complete and a solution was obtained which contained, according to quantitative HPLC analysis, 8.72% by weight (corresponding to 7.53 kg) of 1-(4-chlorophenyl)-3-hydroxypyrazole.

8. Preparation of 1-(4-chlorophenyl)-3-hydroxypyrazole using pure oxygen without catalysis under pressure The solution of 9.75 g of 1-(4-chlorophenyl)pyrazolidin-3-one in 150 g of water was charged into a 300 ml autoclave. Oxygen at 15 bar was then forced in; the mixture was heated to 50° C. and allowed to stand for six hours at this temperature. The mixture was cooled and adjusted to a pH of 5 by adding acetic acid. The solid which precipitated out was filtered off with suction, digested in water for 30 minutes at 60° C., and again filtered off with suction and dried. 9.4 g of the product remained as colorless powder having a content of 95.4%.

9. Preparation of 1-(4-methylphenyl)-3-hydroxypyrazole using pure oxygen without catalysis 25.8 g of 1-(4-methylphenyl)pyrazolidin-3-one were dissolved in a mixture of 10.3 g of potassium hydroxide and 196 g of water. At 60° C., oxygen was passed in in such a manner that it was just completely absorbed. After approximately 90 min, oxygen was no longer absorbed and the reaction mixture was cooled to room temperature. The product was precipitated out with acetic acid, filtered off with suction, washed with water and dried. 21.6 g of a colorless solid remained, m.p. 135–137° C.

10. Preparation of 1-(3,4-dichlorophenyl)-3-hydroxypyrazole using pure oxygen without catalysis 11.8 g of 1-(3,4-dichlorophenyl)pyrazolidin-3-one were dissolved in a mixture of 5.9 g of potassium hydroxide and 113 g of water. At 60° C., oxygen was passed in and the reaction was followed by HPLC. The reaction was complete after approximately 60 min; the mixture was cooled to room temperature and the product was precipitated out with 6 g of acetic acid, filtered off with suction, washed with water and dried. 7.3 g of a colorless solid remained, m.p. 168–170° C.

11. Preparation of 1-(3-chloro-4-fluorophenyl)-3-hydroxypyrazole using pure oxygen without catalysis 47.9 g of 1-(3-chloro-4-fluorophenyl)pyrazolidin-3-one were added to a solution of 21.55 g of potassium hydroxide in 409 g of water and were oxidized at 70° C. by passing in oxygen. After approximately 40 min, the reaction was complete, the mixture was cooled to room temperature and 23 g of acetic acid were added. A slimy solid precipitated out which was successively digested in water and diisopropyl ether and was filtered off with suction. After drying, 39 g of solid remained which was purified by column chromatography on silica gel using cyclohexane. 21 g of the product were obtained, m.p. 157–159° C.

12. Preparation of 1-(4-chlorophenyl)-3-hydroxypyrazole using pure oxygen without catalysis 850 g of a 7.4% strength solution of 1-(4-chlorophenyl)-pyrazolidin-3-one in 5% strength potassium hydroxide solution were heated to 60° C. oxygen was introduced into the solution via a capillary in such a manner that it was just completely absorbed. After approximately 90 min, the reaction was complete according to monitoring by HPLC. 855 g of a solution were obtained which had a 1-(4-chlorophenyl)-3-hydroxypyrazole content of 7.3%.

13. Preparation of 1-(4-chlorophenyl)-3-hydroxypyrazole using pure oxygen with Co(II) catalysis 900 g of a 6.9% strength solution of 1-(4-chlorophenyl)-pyrazolidin-3-one in 5% strength potassium hydroxide solution were admixed with 600 mg of cobalt(II) acetate and oxygen was passed into the solution at room temperature via a capillary in such a manner that it was just completely absorbed. After approximately 30 min, the reaction was complete according to HPLC monitoring, the temperature having increased to 40° C. 908 g of a solution were obtained which had a 1-(4-chlorophenyl)-3-hydroxypyrazole content of 6.7%.

We claim:

1. A process for preparing N-substituted 3-hydroxypyrazoles of the formula I

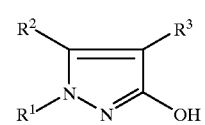

where
$R^1$ is unsubstituted or substituted $C_1$–$C_{10}$-alkyl, $C_2$–$C_{10}$-alkenyl, $C_2$–$C_{10}$-alkynyl, $C_3$–$C_{10}$-cycloalkyl, unsubstituted or substituted aryl selected from phenyl and naphthyl; heteroaryl selected from furyl, thienyl, pyrrolyl, isoxazolyl, isothiazolyl, pyrazolyl, oxazolyl, imidazolyl, pyridyl, pyridazinyl, pyrimidinyl and triazinyl; and $R^2$, $R^3$ are hydrogen, cyano, halogen and unsubstituted or substituted $C_1$–$C_{10}$-alkyl, $C_2$–$C_{10}$-alkenyl, $C_2$–$C_{10}$-alkynyl, $C_3$–$C_{10}$-cycloalkyl; unsubstituted or substituted aryl selected from phenyl and naphthyl; heteroaryl selected from furyl, thienyl, pyrrolyl, isoxazolyl, isothiazolyl, pyrazolyl, oxazolyl, imidazolyl, pyridyl, pyridazinyl, pyrimidinyl and triazinyl;

where the substituents $R^1$, $R^2$ and $R^3$ are inert under the reaction conditions,
by oxidizing a pyrazolidin-3-one of the formula II

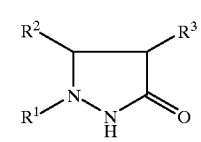

which comprises carrying out the reaction of the water-soluble compounds of the formula II in water in the presence of a base using oxygen as oxidizing agent.

2. A process as claimed in claim 1, wherein $R^1$ is phenyl which can be substituted by the following groups which are inert under the reaction conditions: halogen, cyano, $SO_3H$, COOH, $C_1$–$C_{10}$-alkyl, $C_2$–$C_{10}$-alkenyl or $C_2$–$C_{10}$-alkynyl.

3. A process as claimed in claim 1, wherein $R^2$ is hydrogen.

4. A process as claimed in claim 1, wherein $R^3$ is hydrogen or $C_1$–$C_{10}$-alkyl.

5. A process as claimed in claim 1, wherein a base having a $pK_a>7$ is used.

6. A process as claimed in claim 1, wherein an inorganic base is used.

7. A process as claimed in claim 1, wherein the oxidation of II is carried out in the presence of metal salts.

8. A process as claimed in claim 7, wherein the metal salts are added in catalytic amounts.

9. A process as claimed in claim 7, wherein the metal salt used is an iron salt.

10. A process as claimed in claim 7, wherein the metal salt used is a copper salt.

11. A process as claimed in claim 7, wherein the metal salt used is a cobalt salt.

12. A process as claimed in claim 1, wherein II is oxidized using pure oxygen as oxidizing agent.

13. A process as claimed in claim 7, wherein II is oxidized using atmospheric oxygen as oxidizing agent.

14. A process as claimed in claim 1, wherein II is oxidized at a pressure of from 1 to 50 bar.

* * * * *